United States Patent
Anstice et al.

(10) Patent No.: US 6,313,192 B1
(45) Date of Patent: Nov. 6, 2001

(54) POLYMERIZABLE CEMENT COMPOSITIONS

(75) Inventors: Helen Mary Anstice; Wydchaya Kanchanavasita, both of London; Gavin John Pearson, Reading; Brain Dennis Schottlander; Amy Louise Sherpa, both of London, all of (GB)

(73) Assignee: Davis Schottlander and Davis Limited, Letchworth (GB)

( * ) Notice: Subject to any disclaimer, the term of this patent is extended or adjusted under 35 U.S.C. 154(b) by 0 days.

(21) Appl. No.: 09/341,528

(22) PCT Filed: Jan. 12, 1998

(86) PCT No.: PCT/GB98/00072

§ 371 Date: Sep. 20, 1999

§ 102(e) Date: Sep. 20, 1999

(87) PCT Pub. No.: WO98/30192

PCT Pub. Date: Jul. 16, 1998

(30) Foreign Application Priority Data

Jan. 13, 1997 (EP) .................................................. 97300175

(51) Int. Cl.$^7$ ..................................................... A61K 6/083
(52) U.S. Cl. ......................... 523/116; 523/115; 523/117; 524/549; 524/811
(58) Field of Search .................................. 523/116, 117; 524/549, 494, 811

(56) References Cited

U.S. PATENT DOCUMENTS

| | | |
|---|---|---|
| 4,264,489 | 4/1981 | Ibsen et al. . |
| 4,820,744 * | 4/1989 | Kinbota et al. . |
| 5,063,257 | 11/1991 | Akahane et al. . |
| 5,468,787 * | 11/1995 | Braden et al. . |
| 6,126,922 * | 10/2000 | Rozzi et al. ........................ 523/116 |

FOREIGN PATENT DOCUMENTS 2 107 341 A    4/1983   (GB) .

OTHER PUBLICATIONS

Petrolite Corp. v. Watson (DC DC), Mar. 1957.*

Austenal Logs v. Nobilium, Jun. 1957.*

* cited by examiner

*Primary Examiner*—Peter Szekely
(74) *Attorney, Agent, or Firm*—Pillsbury Winthrop LLP

(57) ABSTRACT

A polymerisable cement composition, particularly for dental and biomedical uses, comprises a mixture of polymerisable monomer materials including between 5 and 95% by weight tetrahydrofurfuryl methacrylate (THFMA), and at least 5% by weight secondary monomer, preferably a dimethacrylate; and active filler material, preferably powdered fluoroaluminosillicate glass, capable of undergoing an acid-base reaction in the presence of water with acid or acid derivative groups in the composition. The composition is conveniently in the form of a resin-modified glass-ionomer cement or a compomer composition. The use of THFMA as a monomer material has a number of advantages. THFMA has low shrinkage on polymerisation, good biological acceptability and advantageous water uptake properties in comparison to other monomer systems. The invention also covers a method of preparing a polymerisable cement, and a method of dental treatment.

27 Claims, 5 Drawing Sheets

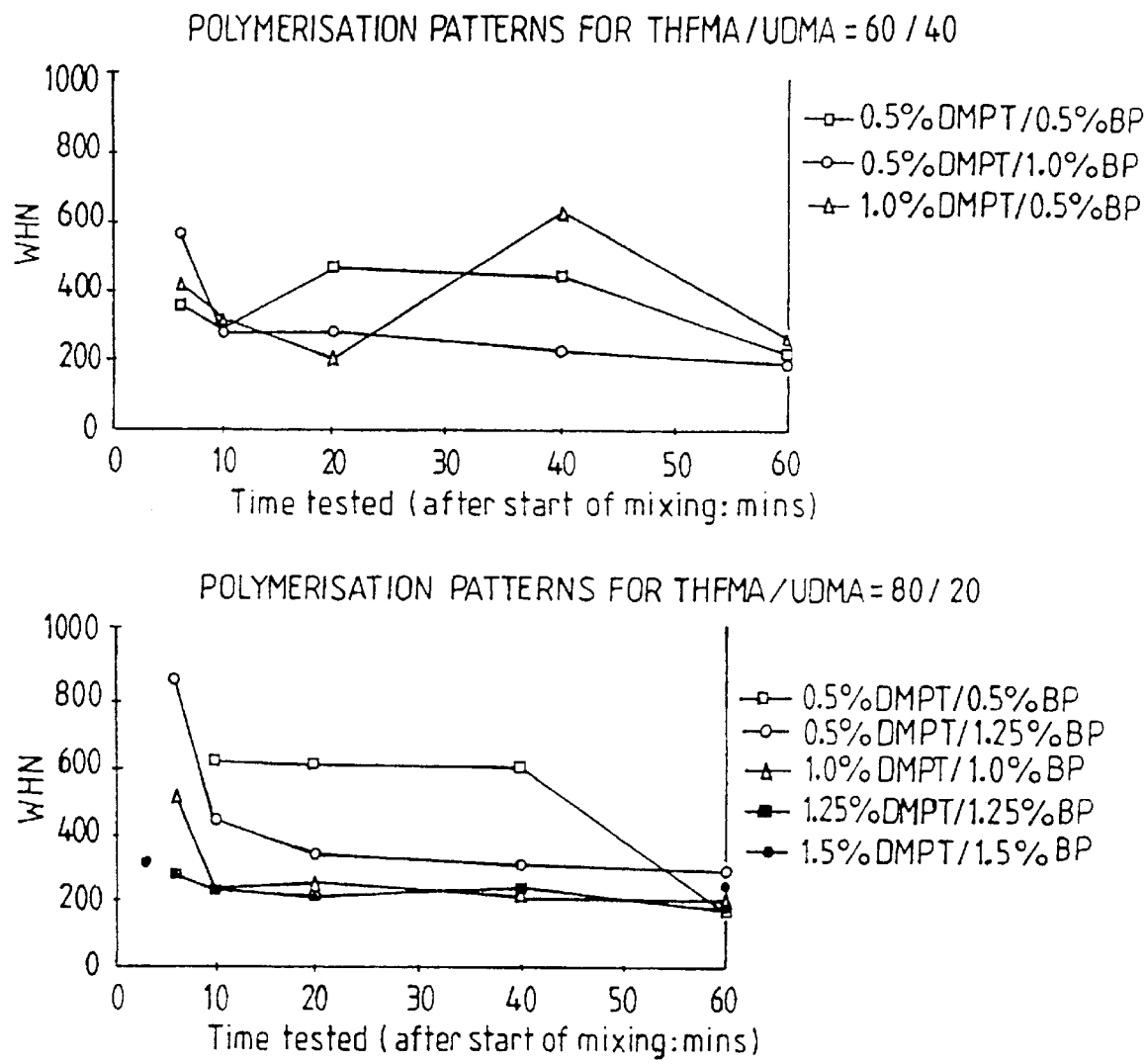
Fig. 3 Sheet 1

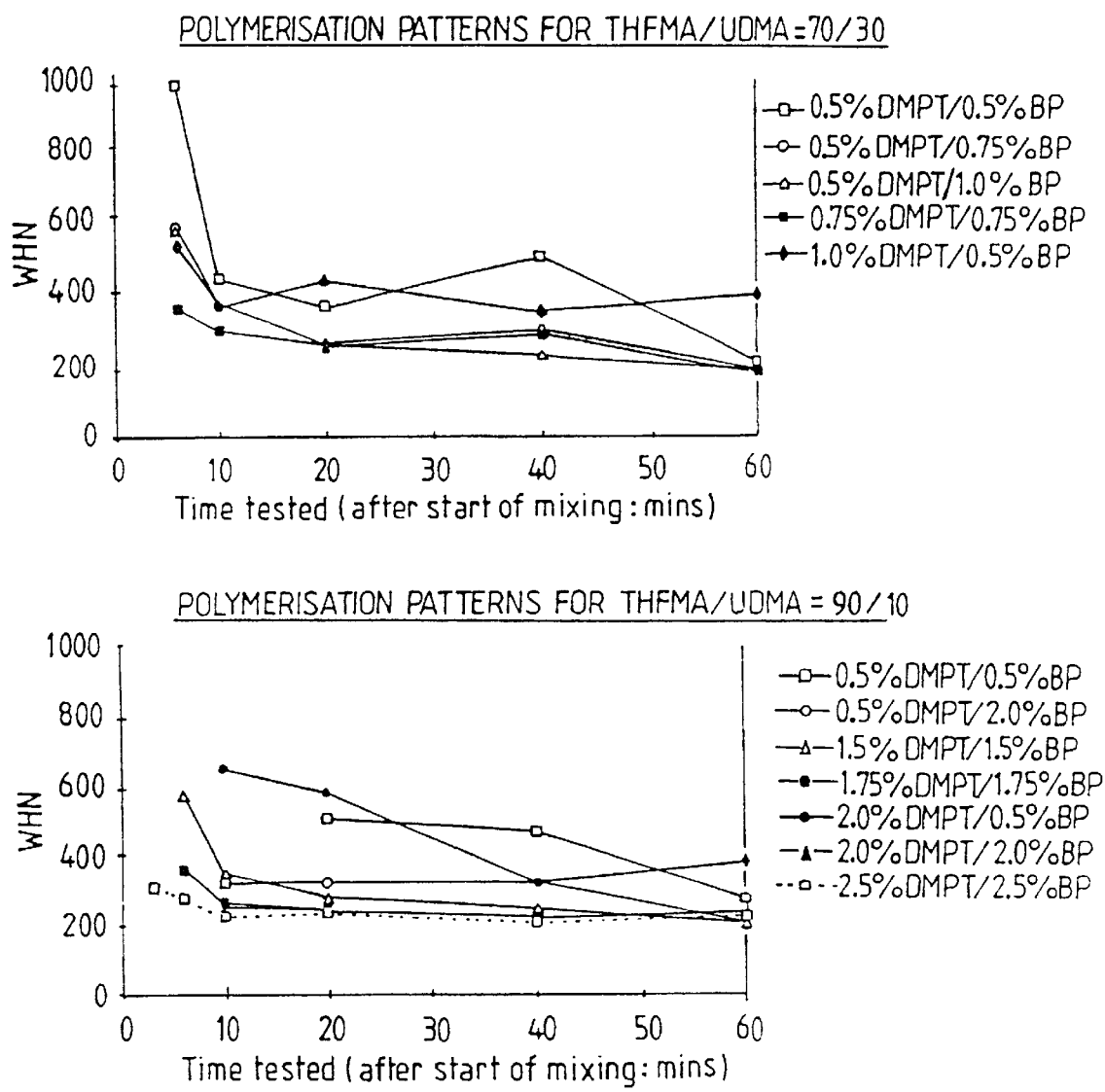
Fig. 3 Sheet 2

POLYMERIZABLE CEMENT COMPOSITIONS

FIELD OF THE INVENTION

This invention concerns polymerisable cement compositions, particularly polymerisable cement compositions suitable for dental and biomedical applications.

BACKGROUND OF THE INVENTION

Cement compositions are widely used in dental and biomedical applications. Typical dental uses include restoration of teeth by filling cavities following destruction by decay, cementing crowns, inlays and orthodontic devices in place, providing a base and/or lining in a tooth cavity etc. A wide range of cement compositions have been developed and are commercially available. These fall into a number of different types.

Glass-ionomer cements are acid-base reaction cements that typically set by the interaction of an aqueous solution of a polymeric acid with an acid-degradable glass,eg as disclosed in GB 1316129. The principal setting reaction is the slow neutralisation of the acidic polymer solution to form a polysalt matrix. The acid is typically a polycarboxylic acid (often polyacrylic acid) and the glass is typically a fluoroaluminosilicate. The setting reaction begins as soon as the components are mixed, and the set material has residual glass particles embedded in interconnected polysalt and silica matrices.

The advantages of glass-ionomer cements include their adhesion to tooth tissue, thus allowing the use of conservative techniques, and sustained fluoride release, thus imparting to the tooth an increased resistance to acid demineralisation.

However the disadvantages associates with glass-ionomer cements are that the immature cement is sensitive to moisture contamination and hence requires protection to ensure optimum final mechanical properties are achieved. The nature of the setting reaction means that the strength of the glass-ionomer develops with time, consequently the immediate strength of the glass-ionomer is not as high as that of other materials. Finally the glass-ionomer is not as tough as some other dental cements.

Composite resin cements set by the free-radical polymerisation of a resin (monomer) component. The cements usually include a non-active filler (usually a glass and/or silica) which is not involved in the setting mechanism of the materials, although the filler is generally bound into the matrix via a difunctional silane coupling agent. The monomers are generally large molecule aromatic or urethane dimethacrylates, selected with the aim of minimising polymerisation shrinkage of the material.

However these monomers have quite high viscosities and consequently smaller dimethacrylate monomers are used as diluents to lower the viscosity and thus increase the capacity for filler incorporation.

Composite resins are supplied as either one or two paste systems, depending upon the method used for initiation of the polymerisation reaction. The reaction may be initiated by an external energy source (one paste) usually high intensity blue light (470nm) eg using an α diketone with an amine reducing agent as the initiator system. Alternatively the polymerisation may be initiated by mixing the components (two paste) with eg a peroxide and tertiary amine as the initiator system.

The advantages of the composite resin are good aesthetics, good mechanical strength nd good wear resistance. However because of the nature of their setting reaction they have the disadvantages of polymerisation shrinkage, polymerisation exotherm, water sorption and monomer leaching. Shrinkage during curing is a particular problem because it allows microleakage around a restoration which can cause further decay of the tooth. It also means that stresses can be set up in the filling or the tooth.

Resin-modified glass-ionomer cements (RMGICs) were introduced with the intention of overcoming the problems associated with the conventional glass-ionomer, eg uncontrolled chemical set and tendency towards brittle fracture, whilst still retaining its advantages, eg fluoride release and adhesion. To achieve this the technologies of the acid-base and resin cements were combined. See, eg, EP 0323120, U.S. Pat. No. 4872936 and U.S. Pat. No. 5154762. One attempt to achieve this advocated simply replacing some of the water in a conventional glass-ionomer cement with a hydrophilic monomer. Another approach also replaced some of the water in the formulation, but in addition modified the polymeric acid so that some of the acid groups were replaced with unsaturated species, so that the polymeric acid could also take part in the polymerisation reaction.

Resin-modified glass-ionomers have two setting reactions: the acid-base reaction of the glass-ionomer, and the polymerisation of the composite resin. The monomer systems used in resin-modified glass-ionomers are not generally the same as those in composite resins. This is because the monomer must be compatible with the aqueous acid-base reaction of the glass-monomer components.

Resin-modified glass-ionomers have the advantage of improved aesthetics compared with conventional glass-ionomers but they also have the potential for fluoride release and the adhesion of the conventional material although it should be noted that some materials are supplied with a bonding agent similar to that used with composite materials. The fracture toughness of the resin-modified material is higher than that of conventional glass-ionomers and in some cases the resin-modified material is higher than that of conventional glass-ionomers and in some cases the resin-containing materials have higher strengths. However, because of the polymerisation reaction involved, resin-modified glass-ionomers have the disadvantages of polymerisation shrinkage and exotherm, water sorption and loss of free monomer. These disadvantages are far more of a problem than they are for composite resins because of the small toxic monomers currently used in resin-modified glass-ionomers.

Acid-modified composite resins (compomers) set by photopolymerisation of their monomer system. However, the systems include monomers with acid character not found in conventional composite resins. The filler in these materials is typically made up, at least in part, of acid-degradable glass as used in glass-ionomers. Consequently, in the presence of water, the monomer should be capable of undergoing a glass-ionomer type reaction with the glass. Unlike conventional and resin-modified glass-ionomer cements, compomers are supplied as one paste systems. To achieve this the water, essential for the acid-base reaction, is excluded from the formulation. Once in situ the cement will take up water.

This water could then initiate the acid-base reaction potentially permitting a glass-ionomer cement style sustained fluoride release from the material. The aesthetics of the compomers are good but their fluoride release rate is lower than that of a glass-ionomer. The bonding system supplied for use with the material assumes that the material will behave like a composite.

The present inventors have carried out experiments to assess alternative monomer materials for use in polymerisable cement compositions, and have discovered that good results are obtained by use of a mixture of monomers including an amount of tetrahydrofurfuryl methacrylate (THFMA).

THFMA is known for use as a monomer material in polymers for a number of purposes, including a composite resin cements for use as provisional or temporary crown-and-bridge resin (WO81/02022 and U.S. Pat. No. 4264489), for use in the construction of dentures, dental bridges and crowns and as bone cements (GB 2107341), and for use in compositions for promoting tissue repair (WO93/09819).

U.S. Pat. No. 5154762 and AU 46717/89 both concern resin-modified glass-ionomer cements employing polymerisable unsaturated organic compounds, particularly various acrylates and methacrylates. These documents refer to a large number of possible polymerisable compounds, including THFMA, but do not include illustrative examples of use of this material and there is no evidence that THFMA has hitherto been used in resin-modified glass-ionomer cements.

In experiments with THFMA, the present inventors have been unable effectively to polymerise 100% THFMA (as broadly disclosed in U.S. Pat. No 5154762 and AU 46717/89) under clinically relevant conditions, but have found that on inclusion of at least 5% by weight of a suitable secondary monomer with the THFMA, polymerisation does occur, and that such monomer mixtures are useful in polymerisable cement compositions for dental and biomedical applications.

SUMMARY OF THE INVENTION

In one aspect, the present invention therefore provides a polymerisable cement composition comprising a mixture of polymerisable monomer materials including between 5 and 95% by weight tetrahydrofurfuryl methacrylate (THFMA), and at least 5% by weight secondary monomer; and active filler material capable of undergoing an acid-base reaction in the presence of water with acid or acid derivative groups in the composition.

Under suitable conditions, the monomer materials polymerise by free radical polymerisation. A number of different initiation systems may be employed for initiating polymerisation, eg as are well known in the prior rt, including cold chemical cure systems eg using benzoyl peroxide (BP) as initiator and NN dimethyl p toluidine (DMPT) as activator and photochemical cure systems eg using camphorquinone (CQ) as initiator and DMPT as activator with exposure to light of suitable wavelength.

Further, the active filler is capable of undergoing acid-base reaction with the acid or acid derivative groups in the presence of water, constituting a second setting mechanism.

The secondary monomer can be any species that is capable of polymerising with or in the presence of THFMA and has biological properties suitable for the intended use of the composition. Suitable materials include acrylates, diacrylates, methacrylates, dimethacrylates, spiroorthocarbonates and ormecers, with currently preferred materials being dimethacrylates including biphenol-A-glycidyl dimethacrylate (BisGMA), urethane dimethacrylate (UDMA) and tri ethylene glycol dimethacrylate (TEGDMA). Mixtures of secondary monomer materials may be used.

The active filler material may be any suitable organic or inorganic filler, eg as are known in the prior art for use in dental cements.

Suitable inorganic active filler materials include metal oxides, metal salts, glasses and ceramics that contain metal compounds, zeolites, and oxidisable metals, as well as products obtained by sintering such materials. Preferred metal oxides include barium oxide, calcium oxide, magnesium oxide and zinc oxide. Preferred metal salts include salts of multivalent cations, for example aluminum acetate, aluminum chloride, calcium chloride, magnesium chloride, zinc chloride, aluminum nitrate, barium nitrate, calcium nitrate, magnesium nitrate, strontium nitrate and calcium fluoroborate. Preferred glasses include borate glasses, phosphate glasses and fluoroaluminosilicate glasses. Fluoroaluminosilicate glasses are particularly preferred as they provide a source of fluoride ions that leach from the filler on reaction with the acid groups, with consequent dental benefits. Mixtures of filler materials may be used.

The active filler material should be in finely divided, particulate or powdered form, for ease of inclusion in the composition, ease of use and ease of reaction. The filler material preferably has an average particle diameter of less than 45 microns.

The active filler material may optionally be surface treated in known manner, including treatment with a polymerisable silane to promote bonding to the resulting polymer, and washing with a dilute acid solution which increases cement hardness (and reduces setting speed).

The active filler material should be present in an amount suitable to provide a composition having good mixing and handling properties before polymerisation and good performance after polymerisation. The filler material conveniently constitutes between 5% and 85% of the total weight of the composition before polymerisation.

The acid or acid derivative groups in the composition may be present in a number of different forms.

For example, the composition may include an acidic polymer, preferably in the form of a homopolymer or copolymer of vinyl phosphonic acid or an alkenoic acid such as acrylic acid, itaconic acid and maleic acid. One currently preferred source of acid groups is polyacrylic acid. Suitable polymers are readily available commercially. The polymer should have an appropriate molecular weight to provide good storage, handling and mixing properties with the molecular weight conveniently being in excess of 5000. A mixture of acidic polymers may be used.

Alternatively, acid groups may be present on one or more of the monomer materials, with such monomers constituting bifunctional molecules containing both acidic and unsaturated species. Suitable bifunctional molecules include those disclosed in U.S. Pat. No. 4872936, eg as described in column 3, lines 5 to 20 and column 3, line 28 to column 4, line 10, and U.S. Pat. No. 5218070, eg as described generally in column 1, line 67 to column 2, line 8, such as butan-1,2,3,4-tetracarboxylic acid, bis (2-hydroxyethyl methacrylate) ester, as described in Example 2.

A mixture of sources of acid groups may be used.

The acid groups should be present in sufficient amount for reaction with the filler material. For example, in embodiments using polyacrylic acid as the source of acid groups and ion-leachable glass as the filler material, satisfactory results have been obtained with glass to acid weight ratio in the range 10:1 to 1:1 preferably 8:1 to 2:1. A glass acid ratio of 4:1 is currently favoured for dental restorative cements.

The composition may optionally include one or more further heterocyclic monomer materials, in addition to THFMA. Suitable heterocyclic monomers include 2.3-epoxypropyl methacrylate, tetrahydropyranyl methacrylate, tetrahydropyran-2-ylmethyl methacrylate, isobornyl methacrylate (IBMA) and tetrahydrofurfurylacrylate. By selection of a suitable mixture of heterocylic monomers, the composition can be tailored to have desired properties suited to particular intended uses thereof.

The THFMA (and other optional heterocyclic monomer material, if present) is preferably present in an amount of at least 30%, more preferably at least 40% by weight of the total weight of the monomer mixture. For mixtures of THFMA/BisGMA, the THFMA content is preferably in the range 65% to 85% by weight; good results have been obtained with a monomer mixture comprising about 70% by weight THFMA and about 30% by weight BisGMA. For mixtures of THFMA/UDMA, the THFMA content is preferably in the range 40% to 80% by weight, and the currently preferred monomer mixtures are 60% by weight THFMA and 40% by weight UDMA and 50% by weight THFMA and 50% by weight UDMA. In three part systems with IBMA replacing some of the THFMA, the preferred percentage of THFMA may be lower than in the two component monomer systems.

The composition may also optionally include non-active filler material, that is filler material that does not undergo an acid-base reaction with the acid groups in the composition under aqueous conditions. Suitable non-active filler materials are known in the prior art, and include quartz powder, microfine silicic acid, aluminum oxide, barium glasses etc. The non-active filler material should be in finely divided form, which may or may not be of comparable particle size to the active filler material. A mixture of non-active filler materials may be used. The number, type and amount of non-active filler materials can be selected in known manner to provide desired properties, eg enhanced mechanical or chemical resistance, radio-opacity etc.

The composition may include water (distilled, deionised or tap water) either included in the compositions as sold or added on use. The amount of water is chosen to provide required handling and mixing properties, and to permit ion transport for the acid-base reaction of the active filler. When included, water is conveniently present in an amount of at least about 1% of the total weight of the composition preferably 3% to 45%, more preferably 3 to 30%.

In some cases, the monomer materials can polymerise without use of a polymerisation initiator, eg by exposure to a high energy pulsed xenon source. However, it is preferred to use in known manner one or more polymerisation initiators that act as a source of free radicals when activated. Such initiators can be used alone or in combination with one or more accelerators, activators and/or sensitisers.

The initiator may be a photoinitiator that promotes polymerisation on exposure to light of a suitable wavelength (eg visible light, ultra violet light, laser light etc) and intensity. The initiator should be sufficiently stable to provide an acceptable shelf life and to permit storage and use under normal dental/biomedical conditions.

Preferred visible light-induced initiators include camphorquinone (which typically is combined with a suitable hydrogen donor such as an amine), diaryliodonium simple or metal complex salts, chromophore-substituted halomethyl-s-triazines and halomethyl oxadiazoles. Particularly preferred visible light-induced photoinitiators include an - diketone, eg. camphorquinone, with a hydrogen donor (such as sodium benzene sulphonate, amines and amine alcohols).

Preferred ultraviolet light-induced polymerization initiators include ketones such as benzyl and benzoin, and acyloins and acylion ethers. Preferred commercially available ultraviolet light-induced polymerization initiators include 2,2-dimethoxy-2-phenylacetophenone (available under the Trade Mark IRGACURE 651) and benzoin methyl ether (2methoxy-2-phenylacetopheneone), both from Ciba-Geigy Corp.

Cold cure (or chemical) initiator systems, not dependent on exposure to heat or light are also known and can be used, eg benzoyl peroxide initiator with NN dimethyl p toluidine activator.

The initiator system ingredients should be present in an appropriate amount to provide the desired rate and extend of polymerisation and are typically present in an amount between 0.01% and 15% of the total weight of liquid, preferably between 0.5% and 5% of this weight. In the filled systems, good results have been obtained with initiator system ingredients each present in the amount 5% by weight of liquid.

The ratio of solid eg powdered materials to liquid materials may be varied and is typically in the range 10:1 to 1:15, preferably 8:1 to 1:1. Good results have been obtained with a solid:liquid ratio of 3:1 for a dental restorative cement.

The composition may include water and/or be mixed with water on use so that both the free radical polymerisation reaction and the acid base reaction take place on use of the composition, in known manner. In this case the composition may be in the form of a resin modified glass ionomer composition (RMGIC). Alternatively, the composition may be in the form of a non-aqueous composition that initially sets on use by the free radical polymerisation reaction and that undergoes a slow acid-base reaction in situ over an extended period of time (in some instances many months) on take-up of water from the surroundings, possibly accompanied by release of fluoride or other useful ions. In this case the composition may be in the form of a compomer composition.

The composition may, for example, be in the form of a two part formulation or a single part, non-aqueous formulation, although other variations are possible.

Various additives may be optionally included in the composition in known manner, such as anti-oxidants, stablizers including UV inhibitors and polymerisation inhibitors, pigments, therapeutic agents such as antibiotics, corticosteroids and other medicinal agents eg metal ions etc.

Compositions in accordance with the invention find application in a range of dental and biomedical uses including use as bone cement. The compositions find particular application in dentistry, including use as a filling material for restoring teeth following destruction by decay and for cementing inlays and crowns into place in a tooth, for providing a base and/or lining in a tooth cavity, for providing temporary fixing of orthodontic devices to teeth and for sealing root canals after endodontic treatment.

The composition is used in conventional manner. In a typical case consisting of a two part RMGIC formulation for use as a dental cement, the two parts are mixed, possibly with addition of an appropriate amount of water, to produce a workable mixture that rapidly becomes putty-like or rubbery in consistency and can be readily used eg by being placed in a tooth cavity. If appropriate, the composition is exposed in situ to a suitable light source to initiate polymerisation. The composition then sets hard in situ in a clinically acceptable time, eg 10 minutes for a dental restorative cement. Maximum hardness may develop over time.

The compositions adhere to teeth via chemical interaction of the acid groups, as with conventional glass-ionomer cement compositions, and as noted above release fluoride ions, if present in the active filler material without degradation of the cement. The properties of the compositions when set, including strength, hardness, etc. are well suited to dental uses.

The use of THFMA as a monomer material has a number of advantages. THFMA has low shrinkage on polymerisation, good biological acceptability and advantageous water uptake properties when compared to other monomer systems.

In a further aspect the invention provides a method of preparing a polymerisable cement, particularly a dental or biomedical cement, comprising mixing the ingredients of the composition of the invention, and causing the mixture to set.

The invention also includes within its scope a method of dental treatment, comprising applying to a tooth a composition in accordance with the invention, and causing the composition to set.

The invention will be further described, by way of illustration, in the following Examples and with reference to the accompanying drawings in which:

FIG. 3 is a series of graphs of Wallace hardness number (WHN) versus time tested (mins) after start of mixing for various mixtures of THFMA/UDMA set using a chemical cure initiator system:

A series of initial experiments were carried out to establish that mixtures of THFMA and secondary monomers, such as BisGMA, polymerise, to investigate different initiator systems and to investigate model RMGIC compositions.

Section 1 - The potentials for auto- and photo-polymerisation of THFMA and monomer mixtures containing THFMA.

EXAMPLE 1 (THFMA and THFMA/BisGMA)

Experiments were carried out with monomers comprising 100% THFMA and mixtures of THFMA with BisGMA in the following weight ratios: 70%/30%, 80%, 20%, 90%, 10% and 95/5%.

The following polymerisation systems were used:
1. Chemical cure (cold cure)
Benzoyl peroxide (BP) - initiator
N.N-dimethyl-p-toluidine (DMPT) - activator
2. Photo-chemical (light cure)
Camphorquinone (CQ) - initiator
N.N-dimethyl-p-toluidine (DMPT) - activator Various combination and amounts of initiators (CQ or BP) and activator (DMPT) were added to the monomer mixtures.

For cold cure, amounts of BP ranging from 0.5% to 5% and amounts of DMPT ranging from 0.5% to 5% were used. For light cure the amount of CQ ranged from 0.5% to 5% and the amount of DMPT was between 0.5 and 10%. In all cases the amounts of initiator and activators are % by weight relative to the total weight of monomer.

The monomers were then poured into a disc-shaped (10mm x 1mm rubber mould and covered with a glass microscope slide, thus reducing oxygen inhibition of the polymerisation reaction. The chemically-cured monomers were allowed to set in the mould for 5 minutes. The photo-initiated monomers were cured for 60s using a Luxor (Luxor is a Trade Mark) visible light-curing unit (from ICI operating at 460–470nm. The set polymers were removed from the mould. Polymerisation of the polymers was arbitrarily determined after 5 minutes by reference to the hardness of the surface of the specimens tested with a spatula: if the surface of the specimen was hard, this indicated that polymerisation had taken place.

Figure 1:
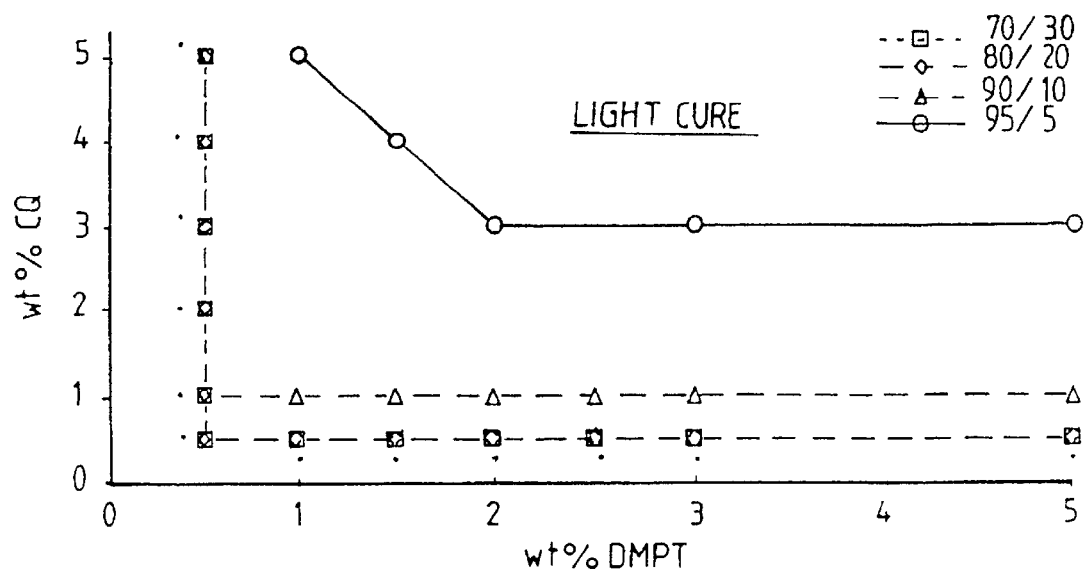
FIG. 1 is a graph of wt% CQ versus wt% DMPT showing minimum level of CQ and DMPT needed to polymerise various THFMA/BisGMA mixtures with asterisks representing coincident points.
Figure 2:
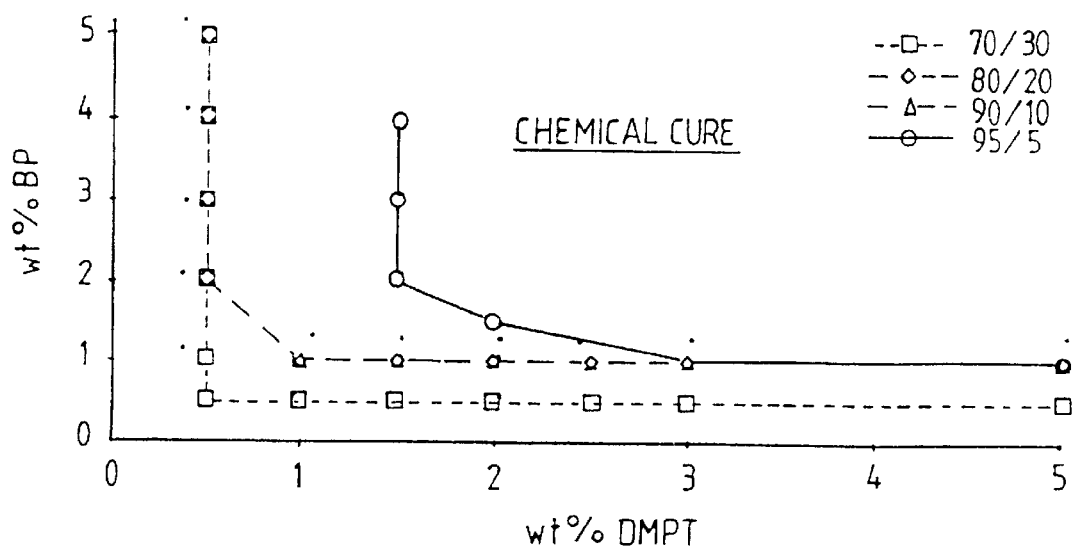
FIG. 2 is a graph similar to FIG. 1 of wt% BP versus wt% DMPT.

With monomer comprising 100% THFMA no polymerisation was obtained with light cure and for cold cure polymerisation was only obtained either using unacceptably high amounts of initiator and activator or in an unacceptably long time scale to be clinically acceptable or useful. However, potentially clinically useful cure regimes were established for all of the THFMA/BisGMA monomer mixtures and results are given in FIGS. 1 and 2.

The following broad conclusions were reached concerning the amounts of initiator and activator.

For photo-initiation for the monomer mixtures THFMA 70%/BisGMA 30% and THFMA 80%/BisGMA 20%, using CQ 0.5% and DMPT 0.5% was sufficient for the polymerisation of the monomer. Mixtures having a lower percentage of BisGMA required higher concentrations of the initiator and activator.

For chemical cure, best polymerisation occurred in the THFMA 70% BisGMA 30% mixture where the lowest concentration of the initiator and activator could be used (BP 0.5% and DMPT 0.5%). Using a lower percentage of BisGMA in the mixture required higher concentrations of the initiator and activator.

In view of the failure of 100% THFMA usefully to polymerise, no further work was carried out on 100% THFMA and further experiments were carried out on mixtures of THFMA with secondary monomers.

EXAMPLE 2 (THFMA/UDMA)

Following the procedure generally as described in Example 1, further experiments were carried out on mixtures of THFMA with UDMA in the following weight ratios: 95%/5%, 90%/10%, 80%/20%, 70%/30%, 60%/40%, 50%/50%, 40%/60%, 30%/70%, 15%/85% and 5%/95%. Both chemical cure (BP/DMPT) and light cure CQ/DMPT systems were used in various amounts, as described in Example 1, although for mixtures containing 50% or more UDMA, the BP or CQ was generally first dissolved in THFMA (a good solvent) and low levels of initiator (0.15 wt%) and activator (2 wt%) were used. The hardness of the resulting specimens was determined using a Wallace microhardness tester. The depth of the impression on a specimen surface is measured and shown on an indicator dial which is graduated into 100 hardness units, each representing a depth of 0.0001 inch. The method of testing is as follows.

A minor load of 1g was applied initially and this was followed by the application of a major load of 300g for 10 seconds. The depth of the resulting indentation was measured with three values per specimen being recorded. Measurements were made 3, 10 and 60 minutes after mixing, the specimens being stored in the interim in darkness at 23°C.

Typical results for chemical cure systems are shown in FIG. 3.

For light cure systems, typical results of average Wallace Hardness number (WHN) at times up to 60 minutes after the start of light curing are as follows:

|  |  | Time (minutes) | | |
| --- | --- | --- | --- | --- |
| % DMPT | % CQ | 3 | 10 | 60 |
| Monomer used: T/U 50/50 | | | | |
| 0.5 | 0.5 | 361 | 270 | 204 |
| 1.0 | 1.0 | 198 | 255 | 205 |
| 2.5 | 2.5 | 154 | 154 | 166 |
| 5.0 | 5.0 | 382 | 322 | 316 |
| Monomer used: T/U 60/40 | | | | |
| 0.5 | 0.5 | 313 | 321 | 427 |
| 1.0 | 1.0 | 224 | 319 | 288 |
| 2.5 | 2.5 | 236 | 205 | 167 |
| 5.0 | 5.0 | 1112 | 672 | 771 |
| Monomer used: T/U 70:30 | | | | |
| 0.5 | 0.5 | C | C | 1384 |
| 1.0 | 1.0 | 1292 | 1500 | 1266 |
| 2.5 | 2.5 | 983 | 602 | 1240 |
| 3.75 | 3.75 | 1197 | 1489 | 1616 |
| 5.0 | 5.0 | 1633 | 1600 | 1596 |

C = specimen retain its shape but is too soft to get a clear WHN reading.

In general it was found that light-cure was improved by lower THFMA content, and chemical-cure improved by higher THFMA content. The optimum monomer mixture is thought to be in the range (THFMA/UDMA) about 50wt%/50wt% to 60wt%/40wt%.

EXAMPLE 3 (THFMA/IBMA/UDMA)

Poly (IBMA) is very brittle, but mixed with THFMA has been shown to lower THFMA's ΔT and increase the time it took to reach maximum temperature ($t_{max}$). IBMA is also relatively non-polar, and has low water absorption characteristics. When mixed with THFMA it could decrease water-sorption and polymerisation shrinkage. The viscosity of IBMA is similar to that of THFMA. Experiments were carried out to investigate the effects on polymerisation patterns of adding IBMA to THFMA/UDMA mixtures.

The various components of a system were mixed. The light-cured systems (light-cured for 60s) were tested for polymerisation and initial Wallace Hardness 2 mins after the start of light-curing. The hardness of the chemical cured systems was monitored until a reading could be obtained. The time was noted as the setting time. In the interval between end of light-curing and testing the specimens were dark-incubated. As a comparison, THFMA/BisGMA (70/30) was tested with 1.0% activator/initiator.

Results for various monomer mixtures were as follows:

The effect of adding IBMA to THFMA/UDMA mixtures

| SYSTEM | T/I/U ratio | CC/LC | % DMPT BP* | % DMPT/ CQ* | set by (mins) [CC] set after 2 mins? [LC] | Mean Initial WHN |
| --- | --- | --- | --- | --- | --- | --- |
| 1 | 80/—/20 | CC | 1.5/1.5 | — | 3 | 298 |
| 2 | 90/—/10 | CC | 2.5/2.5 | — | 4 | 297 |
| 3 | 95/—/5 | CC | 3.5/3.5 | — | 4 | 458 |
| 4 | 50/—/50 | LC | — | 2.5/2.5 | SET | 225 |
| 5 | 60/—/40 | LC | — | 2.5/2.5 | SET | 180 |
| 6 | 64/16/20 | CC | 1.5/1.5 | — | 3 | 295 |
| 7 | 72/18/10 | CC | 2.5/2.5 | — | 4 | 257 |
| 8 | 76/19/5 | CC | 3.5/3.5 | — | 4 | 267 |
| 9 | 40/10/50 | LC | — | 2.5/2.5 | SET | 138 |
| 10 | 48/12/40 | LC | — | 2.5/2.5 | SET | 202 |

* = % total monomer

The addition of the IBMA did not significantly affect the viscosity of the systems.

Standard system for comparison - THFMA/BisGMA=70/30

| SYSTEM | T B ratio | CC LC | % DMPT BP* | % DMPT CQ* | Set by (mins) [CC] Set after 2 mins? [LC] | Mean Initial WHN |
| --- | --- | --- | --- | --- | --- | --- |
| 11 | 70/30 | CC | 1.0/1.0 | — | 3 | 137 |
| 12 | 70/30 | LC | — | 1.0/1.0 | SET | 188 |

* = % total monomer

Replacing 20% of the THFMA content of the THFMA/UDMA mixtures did not significantly affect the setting time or the initial WHN of the systems.

Although the THFMA/BisGMA (70/30) specimens generally produced the best results, systems 5 and 9 (THFMA, UDMA ± IBMA-light-cured) produced specimens with comparable hardness, and the chemically-cured systems 1, 2 and 6 to 8 (THFMA, UDMA ± IBMA) produced acceptable specimens.

EXAMPLE 4 (THFMA/IBMA/BisGMA)

Experiments similar to Example 3 were carried out to investigate mixtures of IBMA/THFMA/BisGMA to ensure that the polymerisation patterns of the monomer mixes were not unduly affected by the addition of IBMA, rather than looking at IBMA as a monomer to enhance the hardness or setting patterns of them. The following monomer mixtures were tested:

| T/B   | 70/30    |
|-------|----------|
| I/T/B | 10/60/30 |
| I/T/B | 20/50/30 |
| T/B   | 80/20    |
| I/T/B | 10/70/20 |
| I/T/B | 20/60/20 |

Method (i) Chemical Cure

The following evaluations were carried out on the mixed material:

a) The time taken to reach the 'jelling' stage (when the liquid mixture begins to look lumpy rather than smooth)

b) The appearance of the mixture at 5 minutes after the start of mixing

Levels of initiator were 1% of the monomer system for both BP and DMPT.

(ii) Light Cure

The specimens were light-cured for 60s. At 2 mins after the start of light-curing, each specimen was examined to assess whether polymerisation had been achieved.

Basic composition of systems:

|         | %  | g      |
|---------|----|--------|
| Monomer | 98 | 0.4900 |
| CQ/BP   | 1  | 0.0050 |
| DMPT    | 1  | 0.0050 |

Results (i) Chemical Cure a) Time taken to reach 'jelling' stage

| MONOMER        | JELLING STARTED (s) |
|----------------|---------------------|
| T/B 70/30      | 90                  |
| I/T/B 10/60/30 | 120                 |
| I/T/B 20/50/30 | 90                  |
| T/B 80/20      | 155                 |
| I/T/B 10/70/20 | 125                 |
| I/T/B 20/60/20 | 120                 | b) Appearance of system at 5 mins after start of mixing

At 5 mins after the start of mixing, all the systems had set to a clear, hard and almost colourless material.

in small amounts, IBMA thus does not significantly affect the setting times using chemical cure when added to THFMA/BisGMA mixtures.

(ii) Light Cure

At 2 mins after the start of light-curing, all systems had set to a clear, hard material - slightly yellow around the edge of the specimens.

IBMA thus does not affect ability of the specimens to polymerise after 60s of light-curing.

Section 2 - The effects of the incorporation of active and non-active fillers on the polymerisation of monomer systems.

EXAMPLE 5 (THFMA/BisGMA)

Mixtures of THFMA and BisGMA monomers were used as in Example 1, that is with ratios 70%/30%, 80%/20%, 90%/10% and 95%5%. The various monomer mixtures were mixed with either powdered ion-leachable fluoroaluminosilicate glass (active filler) or non-active filler material. Various combination of initiators (CQ or BP) and activator (DMPT) were added to the mixtures. Disc specimens were prepared as described previously.

The glass used was obtained from the commercial glass ionomer cement Opusfil W (Opusfil W is a Trade Mark) from Davis Schottlander & Davis Limited using the normal set formulation. Opusfil W is supplied as a powder which contains both glass and a dried form of polymeric acid. To obtain the glass alone for use in these experiments, the acid must be removed from the powder. This was achieved by "washing" the powder with an excess of methanol. The acid dissolves into the methanol, and the glass is then filtered out of the solution. This process is repeated until all the acid has been removed. The glass is then washed with an excess of distilled water to remove any trace of acid. Finally the glass is allowed to dry and then sieved (sieve about 150$\mu$m) to break down any agglomerates.

The non-active filler was an $SiO_2$, $BaO$, $B_2O_3$, $Al_2O_3$ glass of median particle size 0.78$\mu$m (from Schott, Landshut, Germany).

The chemically-cured monomers were allowed to set in the mould for 5 minutes. The photo-initiated monomers were cured for 60s using a light-curing unit. The set specimens were removed from the mould. The polymerisation of the specimens was arbitrarily determined by the surface hardness as in Example 1.

Incorporation of either the glass or the filler required greater concentration of the initiator and activator to achieve polymerisation of most of the monomer mixtures, but the 70/30 THFMA/BisGMA mixture was only slightly affected by the presence of glass or filler.

Section 3 - Investigation of the setting reaction of experimental RMGICs.

EXAMPLE 6 (THFMA/BisGMA, HEMA/BisGMA, HEMA)

A model glass-ionomer system was established, using polyacrylic acid (having a molecular weight in the range 40,000 to 55,000), distilled water and powdered ion-leachable fluoroaluminosilicate glass. The glass was as described in Example 5.

A system comprising glass:acid of 4:1 and powder:liquid of 3:1 was selected as convenient for further testing.

Figure 4:
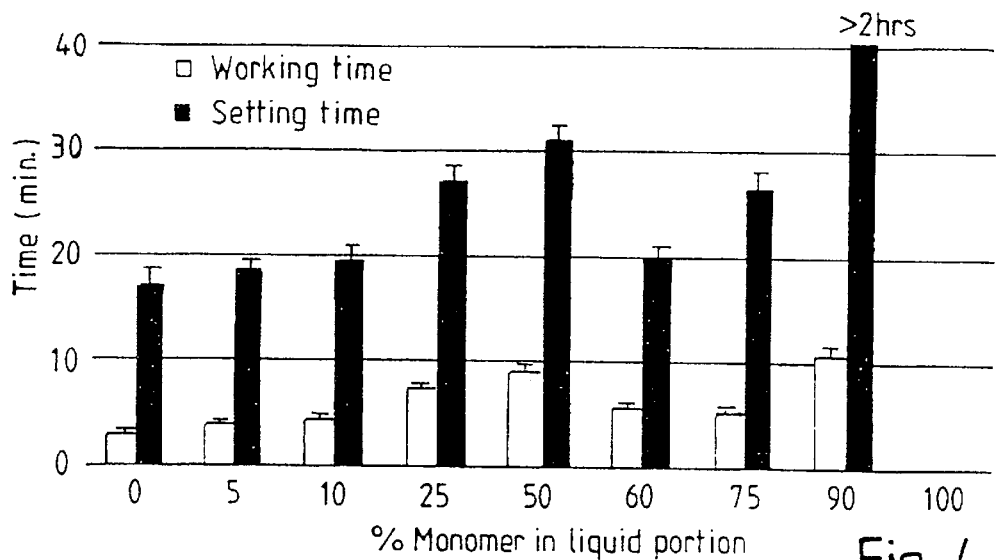
FIG. 4 is a bar chart of time in minutes versus % of (70/30 T/B) monomer in liquid (monomer/water) portion, showing the effect of monomer concentration on working and setting times of cement compositions.

Further experiments were carried out to test the effect in such a system of replacement of the distilled water with increasing percentages of monomer mixture (THFMA:BisGMA 70:30) (10% to 100% in steps of 10%) on the acid-base reaction. The effect of the presence of monomer was monitored by the changes in working and setting times of the cement. As expected, the presence of the monomer increased the working and setting times of the cements, and results are shown in FIG. 4. From these results it was concluded that an optimum monomer concentration that could be used in cement composition would not be in excess of 50 wt% of the liquid.

Section 4 - The effect of the concentration of initiators and activators on the hardness of model RMGIC specimens.

EXAMPLE 7 (THFMA/BisGMA)

Further experiments were carried out using model RMGIC systems, generally as described in Example 6, using the same glass and polyacrylic acid.

The glass was mixed with polyacrylic acid in the weight ratio of 4 to 1 (G:A=4:1). The powder mixtures were then mixed with a liquid mixture of distilled water 50% and monomer (THFMA 70%/BisGMA 30%) 50% in the weight ratio of 3:1 (P:L=3:1). (This represents the maximum concentration of monomer that produced a workable cement). The mixtures were cured either by light cure or cold cure using the initiators and activators in various combinations and amounts as described in Example 1. The hardness of the specimens were determined using the Wallace hardness tester, as described in Example 2.

Figure 5:
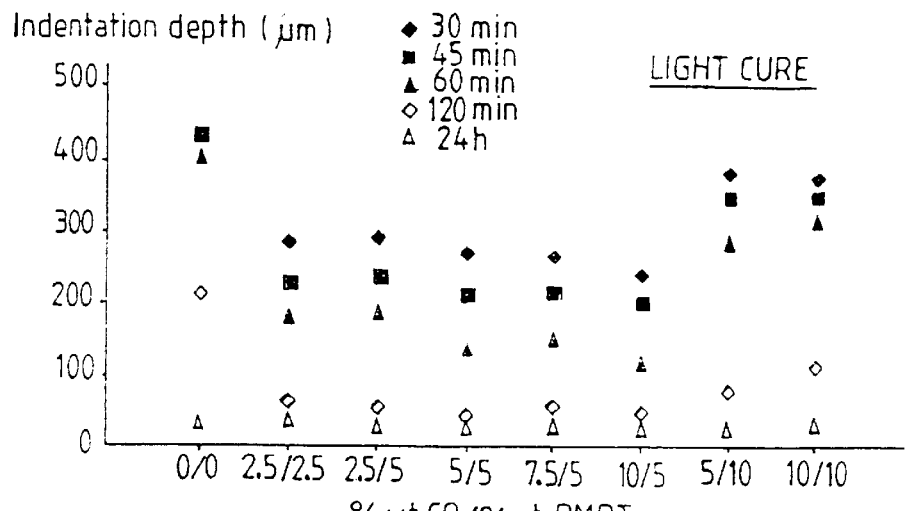
FIG. 5 is a graph of indentation depth ($\mu$m) versus % wt CQ/% wt DMPT with results at different times after mixing.
Figure 6:
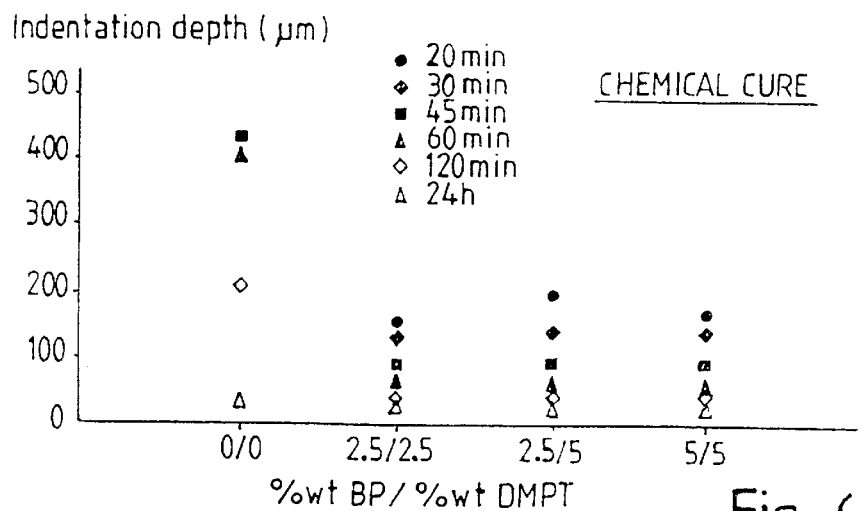
FIG. 6 is a graph of indentation depth ($\mu$m) versus % wt BP/% wt DMPT with results at different times after mixing.

Results are shown in FIG. 5 for light cure and FIG. 6 for chemical cure.

Up to 24h, all specimens polymerised using the initiator/activator system were significantly harder at the corresponding time than the cement set by acid-base reaction alone, i.e. 0.0 wt% initiator/activator concentration. The hardness of all the specimens also increased with time.

For light cure (photoinitiation), there were no significant differences for the hardness of the specimens when the concentration of the initiator (CQ) and the activator (DMPT) were 2.5/2.5, 2.5/5.0, 5.0/5.0, 7.5/5.0 and 10.0/5.0%. The hardnesses were less when the concentrations increased over this level.

For cold cure (chemical cure), there were no significant differences for the hardness of the specimens when the concentrations of the initiator (BP) and the activator (DMPT) were 2.5/2.5, 2.5/5.0, and 5.0/5.0%.

Section 5 - The effects of non-active filler content on hardness of model RMGIC specimens.

EXAMPLE 8 (THFMA BisGMA)

Further experiments were carried out using model RMGIC systems, generally as described in Example 6, using the same glass and polyacrylic acid.

Figure 7:
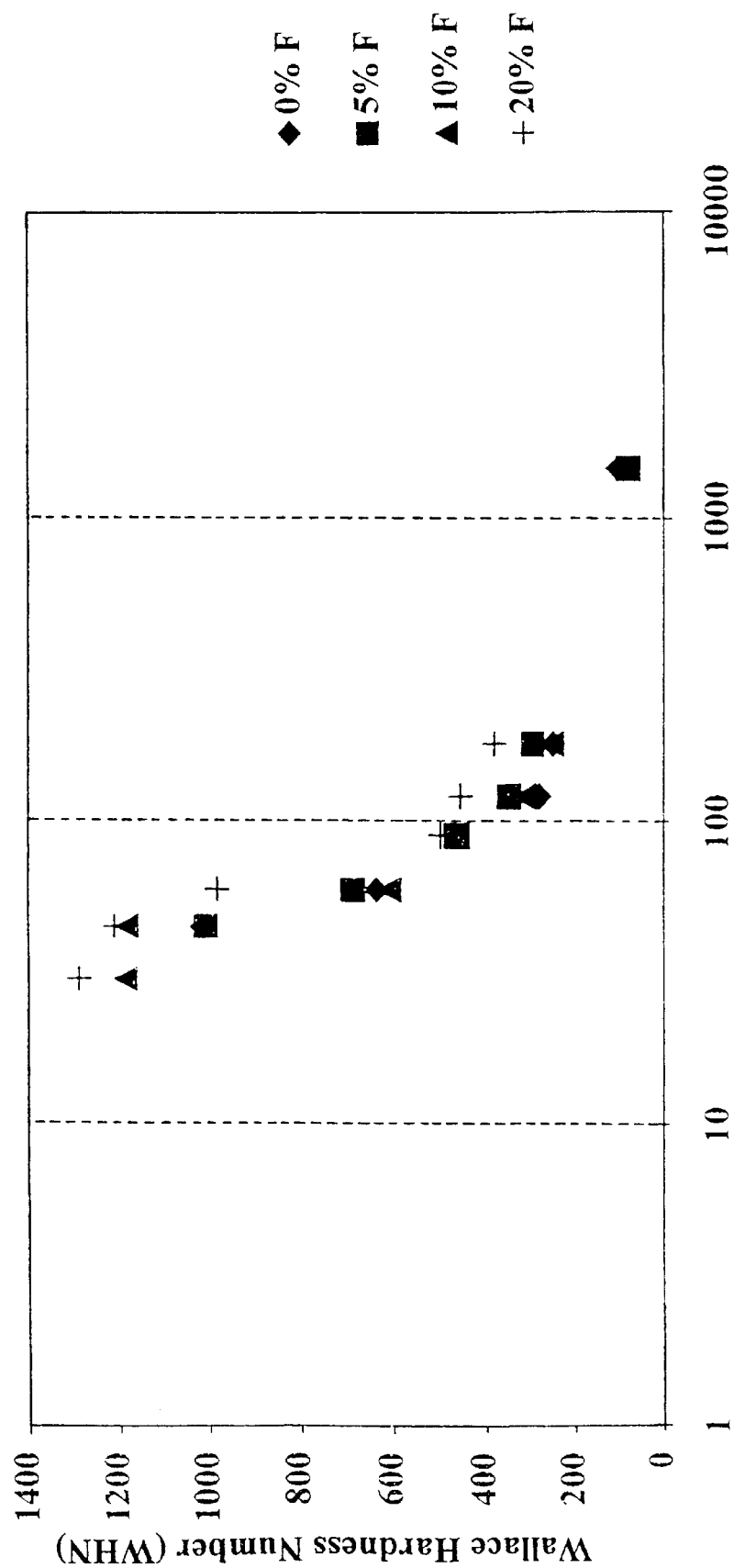
FIG. 7 is a graph of Wallace hardness number (WHN) versus time tested after mixing (mins) for various experimental RMGICs including non-active filler (F) in different amounts.

The glass was mixed with polyacrylic acid in the weight ratio of 4 to 1 (G/A=4:1). Non-active filler material, as in Example 5, was then added at amounts of 0%, 5%, 10%, 15% and 20% as a % by weight of the total weight of the powder. The mixtures were then mixed with a mixture of distilled water 80% and monomer (THFMA 70% and BisGMA 30%) 20% in the weight ratio of 3:1 (P/L=3.1). Both light cure and dark cure systems were used. The hardness of the specimens were determined using the Wallace hardness tester, as described in Example 2. Results are given in FIG. 7, which shows the hardness of the specimens was not adversely affected by the presence or amount of filler.

Section 6 - Dental cement formulations

EXAMPLE 9

Prototype RMGIC formulations are as follows:

|  | Light-cured only % by weight | Light-cure & chemical cure % by weight |
|---|---|---|
| LIQUID |  |  |
| THFMA | 6.9 | 6.7 |
| BisGMA | 2.9 | 2.9 |
| Water | 14.7 | 14.4 |
| DMPT | 0.5 | 1.0 |
| POWDER |  |  |
| Glass | 59.5 | 59.1 |
| Polyacid | 15.0 | 14.9 |
| CQ | 0.5 | 0.5 |
| BP | — | 0.5 |

Ingredients are dispensed and mixed either mechanically or by hand.

Glass and polyacid are as described in previous examples.

What is claimed is:

1. A polymerisable cement composition, comprising a mixture of polymerisable monomer materials including between 5 and 95% by weight tetrahydrofurfuryl methacrylate (THFMA), and at least 5% by weight secondary monomer, said mixture of monomer materials including acid groups; and active filler material capable of undergoing an acid-base reaction in the presence of water with said acid groups in the composition.

2. A composition according to claim 1, wherein the secondary monomer is one or more species capable of polymerising with or in the presence of THFMA and having biological properties suitable for the intended use of the composition.

3. A composition according to claim 2, wherein the active filler is powdered fluoroaluminosilicate glass.

4. A composition according to claim 1, comprising polyacrylic acid as a source of acid groups.

5. A composition according to claim 4, including ion-leachable glass as the filler material, wherein the weight ratio of glass:acid is in the range 10:1 to 1:1.

6. A composition according to claim 1 comprising one or more further heterocyclic monomer materials.

7. A composition according to claim 1 further comprising non-active filler material.

8. A composition according to claim 1 or claim 6 wherein the THFMA and any further heterocyclic monomer material present comprise at least 30% by weight of the monomers.

9. A composition according to claim 1, wherein the monomers comprise THFMA and BisGMA with the THFMA content being in the range 65% to 85% by weight of the weight of the monomers.

10. A composition according to claim 9, wherein the monomers comprise about 70% by weight THFMA and about 30% by weight BisGMA.

11. A composition according to claim 1, wherein the monomers comprise THFMA and UDMA, with the THFMA content being in the range 50% to 60% by weight of the weight of the monomers.

12. A composition according to claim 1, including water in an amount of at least about 1% by weight of the total weight of the composition.

13. A composition according to claim 1, comprising one ore more polymerisation initiators.

14. A composition according to claim 13, comprising one or more photoinitiators.

15. A composition according to claim 13, comprising one or more chemical initiators.

16. A composition according to claim 13, 14 or 15, further comprising one or more accelerators, activators and/or sensitisers.

17. A composition according to claim 13 wherein initiator is present in an amount up to about 15% by weight of liquid.

18. A composition according to claim 1, in the form of a resin-modified glass-ionomer composition or a compomer composition.

19. A method of preparing a polymerisable cement comprising mixing the ingredients of the composition of claim 1 and causing the mixture to set.

20. A method of dental treatment, comprising applying to a tooth a composition in accordance with claim 1 and causing the composition to set.

21. A composition according to claim 1 wherein the secondary monomer is at least one monomer selected from the group consisting of bisphenol-A-glycidyl dimethacrylate (BisGMA), urethane dimethacrylate (UDMA) and tri ethyl glycol dimethacrylate (TEGDMA).

22. A composition according to claim 5 wherein the weight ratio of glass:acid is in the range 8:1 to 2:1.

23. A composition according to claim 6 wherein said further heterocyclic monomer material is selected from the group consisting of 2,3-epoxypropyl methacrylate, tetrahydropyranyl methacrylate, tetrahydropyran-2-ylmethyl methacrylate, isobornyl methacrylate (IBMA) or tetrahydrofurfuryl acrylate.

24. A composition according to claim 8 wherein the THFMA and any further heterocyclic monomer material present comprise at least 40% by weight of the monomers.

25. A composition according to claim 12 including water in an amount of from 3 to 30% by weight of the total weight of the composition.

26. A composition according to claim 1 wherein the acid groups are present as part of the secondary monomer or as a separate component of said composition.

27. A polymerisable cement composition, comprising a mixture of polymerisable monomer materials including between 5 and 95% by weight tetrahydrofurfuryl methacrylate (THFMA), and at least 5% by weight secondary monomer, said composition including acid groups present as a separate component; and active filler material capable of undergoing an acid-base reaction in the presence of water with said acid groups in the composition.

* * * * *